United States Patent [19]

Ohashi et al.

[11] 4,376,818
[45] Mar. 15, 1983

[54] NOVEL HARDENER FOR GELATIN AND METHOD FOR HARDENING GELATIN

[75] Inventors: Minoru Ohashi; Katsuaki Iwaosa, both of Nagaokakyo, Japan

[73] Assignee: Mitsubishi Paper Mills, Ltd., Tokyo, Japan

[21] Appl. No.: 179,784

[22] Filed: Aug. 20, 1980

[30] Foreign Application Priority Data

Aug. 31, 1979 [JP] Japan .................................. 54/111581

[51] Int. Cl.³ ............................................... C09H 7/00
[52] U.S. Cl. .................................... 430/623; 106/125; 260/117; 430/621
[58] Field of Search ................ 260/117; 430/623, 621; 106/125

[56] References Cited

U.S. PATENT DOCUMENTS

| | | | |
|---|---|---|---|
| 4,057,538 | 11/1977 | Habu et al. | 260/117 |
| 4,066,636 | 1/1978 | Sera et al. | 260/117 |
| 4,067,741 | 1/1978 | Bergthaller et al. | 260/117 X |
| 4,096,137 | 6/1978 | Sera et al. | 260/117 |
| 4,111,926 | 9/1978 | Sera et al. | 260/117 |
| 4,254,217 | 3/1981 | Ohashi et al. | 430/623 |

*Primary Examiner*—Howard E. Schain
*Attorney, Agent, or Firm*—Cushman, Darby & Cushman

[57] ABSTRACT

Compounds represented by the following general formula are used as hardeners for gelatin, in particular gelatin layers of photographic light sensitive materials

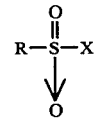

(wherein R and X are the same as defined in the specification).

19 Claims, No Drawings

NOVEL HARDENER FOR GELATIN AND METHOD FOR HARDENING GELATIN

BACKGROUND OF THE INVENTION

This invention relates to a novel hardener for hardening gelatin, especially gelatin films of photographic light sensitive materials and a method for hardening gelatin with said hardener.

Generally, photographic light sensitive materials comprise a suitable support such as glass, paper, synthetic resin film, etc. on which are coated various layers such as silver halide emulsion layers, filter layers, interlayers, protective layers, undercoat layers, backcoat layers, ultraviolet absorbing layers, antihalation layers, etc. These constitutive layers comprise the so-called gelatin films mainly composed of gelatin.

Therefore, properties of these constitutive layers depend mainly on properties of gelatin. The properties of gelatin per se such as low melting point, excessive water swelling, low mechanical strength, etc. are fatal defects as properties of constitutive layers of photographic light sensitive materials.

Therefore, hitherto, efforts have been made to improve the properties of gelatin by reacting gelatin with various hardeners to cause crosslinking reactions with functional groups in gelatin molecules such as amino group, carboxyl group, amide group, etc. Many compounds have been known to be effective for hardening gelatin to increase water resistance, heat resistance and scratch resistance of gelatin layers. Examples of these hardeners are aldehyde compounds such as formaldehyde, glutaraldehyde, etc., compounds having reactive halogens as disclosed in U.S. Pat. Nos. 3,288,775, and 2,732,303, British Pat. Nos. 974,723 and 1,167,207, etc., ketone compounds such as diacetyl cyclopentanedione, bis(2-chloroethyl urea), 2-hydroxy-4,6-dichloro-1,3,5-triazine, divinyl sulfone, 5-acetyl-1,3-diacryloylhexahydro-1,3,5-triazine, compounds having reactive olefins as disclosed in U.S. Pat. Nos. 3,635,718 and 3,232,763 and British Pat. No. 994,809, N-methylol compounds as disclosed in U.S. Pat. Nos. 2,732,316, 2,586,168, etc., isocyanates as disclosed in U.S. Pat. No. 3,103,437, aziridine compounds as disclosed in U.S. Pat. Nos. 3,107,280, 2,983,611, etc., acid derivatives as disclosed in U.S. Pat. Nos. 2,725,294, 2,725,295, etc., carbodiimide compounds as disclosed in U.S. Pat. No. 3,100,704, etc., epoxy compounds as disclosed in U.S. Pat. No. 3,091,537, etc., isoxazole compounds as disclosed in U.S. Pat. Nos. 3,321,313, 3,543,292, etc., halogenocarboxyaldehydes such as mucochloric acid, dioxane derivatives such as dihydroxydioxane, dichlorodioxane, etc., inorganic hardeners such as chrome alum, zirconium sulfate, chromium trichloride, etc. However, all of these known hardeners may have any of the following defects when used in photographic light sensitive materials, for example, insufficient hardening action; change of hardening effect with lapse of a long time period called "after-hardening" caused by slow hardening reaction with gelatin; adverse effects on properties of photographic light sensitive materials (especially, increase of fog, reduction of sensitivity, softening of tone, decrease of maximum density, etc.); loss of hardening action caused by other coexisting photographic additives; decrease of effects of other photographic additives (e.g., couplers of color emulsions); formation of stains; difficulty in preparation of the compounds per se in a large amount; poor preservability due to instability of the hardeners per se; etc.

Recently, rapid processing of photographic light sensitive materials has become necessary and improvements for this purpose and improvements of processing solutions suitable for use for such photographic materials have been made. For example, for rapid penetration of processing solution, amount of gelatin in photographic light sensitive materials has been reduced and moreover the layers have been made thin. However, the reduction in the amount of gelatin and making the layers thin cause not only deterioration of film properties, but increase of fog. Thus, because of spread of high temperature and rapid processing by automatic processors and strong processing solutions, films having high mechanical strength and having properties not damaging their photographic characterisics are demanded.

SUMMARY OF THE INVENTION

It is an object of this invention to provide a novel hardeners having no such defects as mentioned above and another object of this invention is to provide a method for hardening gelatin, especially gelatin films of photographic light sensitive materials with said novel hardener. Other objects and advantages of this invention will become apparent from an examination of the specification and claims which follow.

DESCRIPTION OF THE INVENTION

The above objects of this invention are attained by using the compounds represented by the following general formula as hardeners for gelatin.

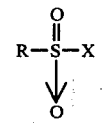

where R represents an alkyl group of preferably $C_{1-5}$ or aryl group and X represents an oxy group represented by $-O-R_1$, an azole group represented by

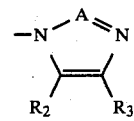

or its quaternary salt represented by

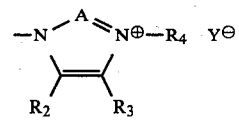

wherein $R_1$ is an amino group represented by

a group represented by

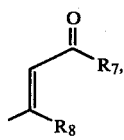

a pyridinium group represented by

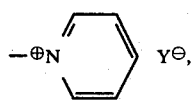

a pyridyl group represented by

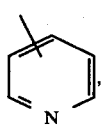

a quinolyl group represented by

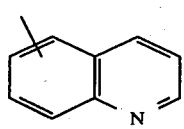

or a quaternary salt thereof represented by

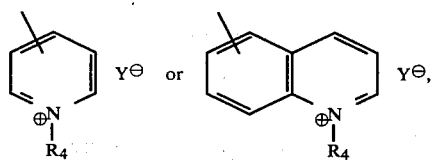

these pyridinium group, pyridyl group and quinolyl group may be optionally substituted with alkyl of preferably $C_{1-5}$, aryl, aralkyl, e.g., benzyl, phenethyl, etc., carboxyl or sulfo group, $Y^\ominus$ is not present when they are substituted with carboxyl group, sulfo group or group containing carboxyl or sulfo group, A is nitrogen atom or carbon atom and when A is carbon atom this carbon atom may have substituent alkyl of preferably $C_{1-5}$, $R_2$ and $R_3$ are hydrogen atom, alkyl group of preferably $C_{1-5}$ or aryl group and may form a ring together, $R_4$ is an alkyl group of preferably $C_{1-5}$ or aralkyl group, e.g., benzyl, phenethyl, etc., and when $R_4$ contains sulfo group or carboxyl group, $Y^\ominus$ is not present and $Y^\ominus$ is an anion (in which $R_5$ and $R_6$ are alkyl group of preferably $C_{1-5}$ or acyl group and may form a ring together, $R_7$ and $R_8$ are alkyl group of preferably $C_{1-5}$, aryl group or aralkyl group, e.g., benzyl, phenethyl, etc., and may form a ring together and $R_4$ and $Y^\ominus$ are same as above).

The following are specific examples of the compounds represented by said general formula which never limit the invention.

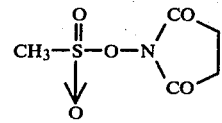 (1)

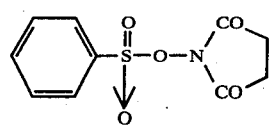 (2)

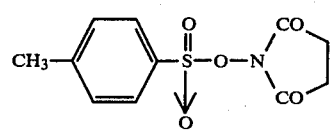 (3)

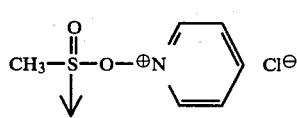 (4)

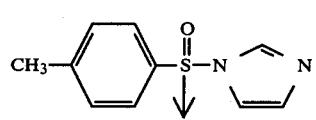 (5)

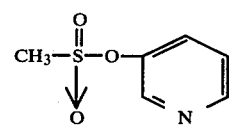 (6)

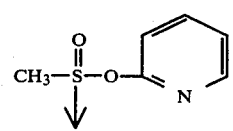 (7)

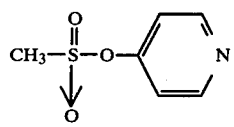 (8)

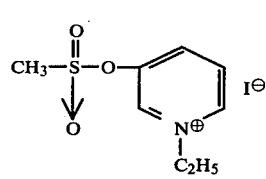 (9)

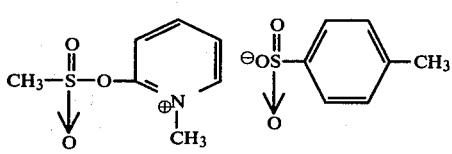 (10)

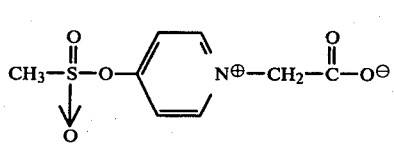 (11)

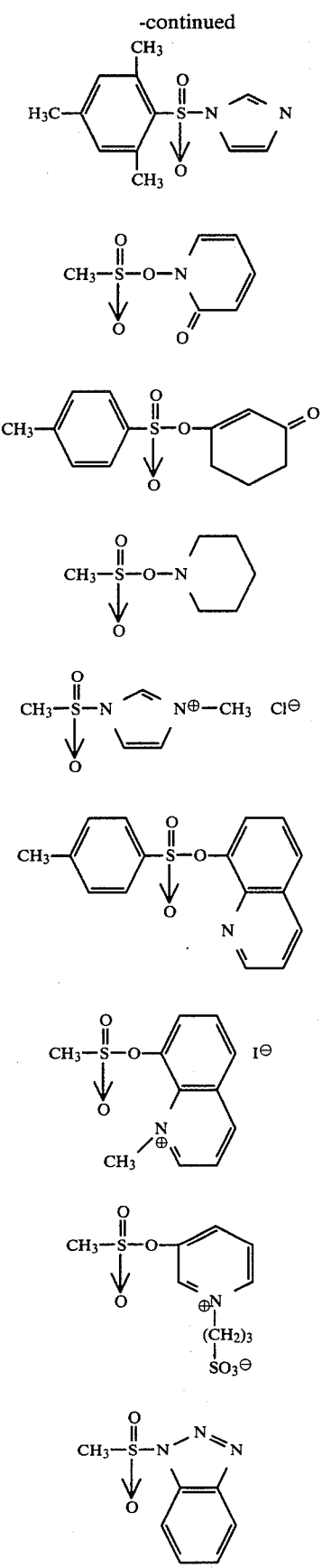
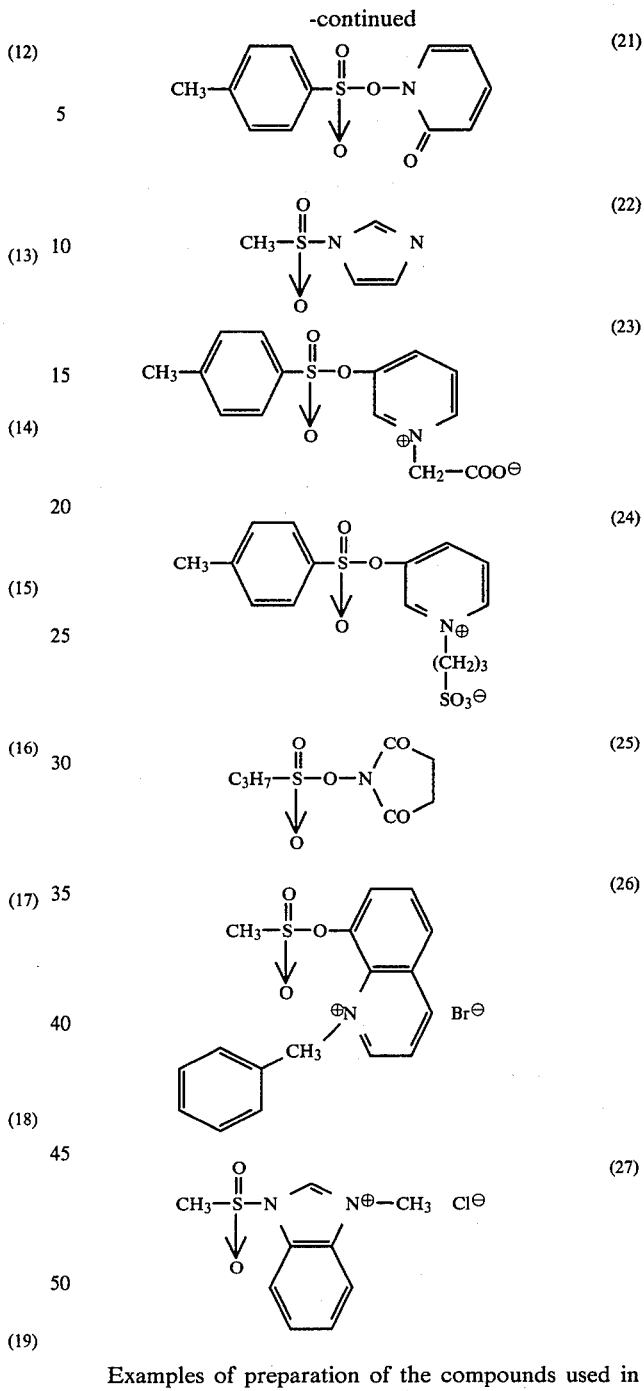

Examples of preparation of the compounds used in this invention will be shown below.

PREPARATION EXAMPLE 1

[Compound (1) exemplified above]

5.8 g of N-hydroxysuccinimide was dissolved in 40 ml of dioxane. To the resultant solution was added 5.6 g of triethylamine and then further added little by little with stirring 6.3 g of methanesulfonyl chloride and then this solution was stirred for one day at room temperature. After reaction the precipitated salt was filtered off and the filtrate was concentrated under reduced pressure to obtain a residue, which was recrystallized from 100 ml of water.

Yield 6.3 g Melting point 152°–153° C.

Elemental analysis—Calcd.—C: 31.09%, H: 3.65%, N: 7.25%. Found—C: 31.20%, H: 3.55%, N: 7.41%.

PREPARATION EXAMPLE 2

[Compound (4)]

6.3 g of methanesulfonyl chloride was dissolved in 50 ml of acetone. Then, temperature of this reaction solution was lowered to about 10° C. and 4.75 g of pyridine-N-oxide was added thereto little by little. After completion of the addition, reaction was effected at room temperature for 2 hours. After the reaction, the solvent was concentrated under reduced pressure and ethyl acetate was added to precipitate crystals, which were filtered and washed with ethyl acetate. The resultant crystals were recrystallized from 150 ml of acetone to obtain 6.7 g of the compound (4) which had a melting point of 101°–103.5° C.

Elemental analysis—Calcd.—C: 34.37%, H: 3.85%, N: 6.68%. Found—C: 34.55%, H: 3.85%, N: 6.70%.

PREPARATION EXAMPLE 3

[Compound (6)]

4.75 g of 3-hydroxypyridine was dissolved in 50 ml of dioxane. Then, 5.6 g of triethylamine was added to the solution and 6.3 g of methanesulfonyl chloride was added dropwise thereto. After completion of the addition, reaction was carried out at room temperature for 3 hours. After completion of the reaction, the precipitated salt was filtered off and filtrate was concentrated under reduced pressure. 30 ml of benzene was added thereto and recrystallization was effected to obtain 6.2 g of compound (6) which had a melting point of 51°–53° C.

Elemental analysis—Calcd.—C: 41.61%, H: 4.07%, N: 8.09%. Found—C: 41.30%, H: 4.15%, N: 8.01%.

PREPARATION EXAMPLE 4

[Compound (7)]

Compound (7) was obtained in the same manner as Preparation Example 3 except that 3-hydroxypyridine was replaced by 2-hydroxypyridine.

Yield 6.0 g Melting point 47°–48° C.

Elemental analysis—Calcd.—C: 41.61%, H: 4.07%, N: 8.09%. Found—C: 41.75%, H: 4.20%, N: 8.01%.

PREPARATION EXAMPLE 5

[Compound (9)]

To 8.7 g of the compound (6) obtained in Preparation Example 3 was added 20 ml of ethyl iodide to dissolve the compound and the solution was heated at 75° C. for 30 minutes to precipitate crystal, which was filtered out, washed well with benzene and dried.

Yield 7.3 g Melting point 151°–152° C.

Elemental analysis—Calcd.—C: 29.19%, H: 3.67%, N: 4.26%. Found—C: 29.30%, H: 3.70%, N: 4.16%.

PREPARATION EXAMPLE 6

[Compound (20)]

6.0 g of benzotriazole was dissolved in 35 ml of dioxane. Then, 5.6 g of triethylamine was added thereto and 6.3 g of methanesulfonyl chloride was further added little by little. After completion of the addition, this was stirred at room temperature for one hour. After reaction, the precipitated salt was filtered off and filtrate was concentrated under reduced pressure and recrystallized from 60 ml of benzene to obtain 9.4 g of compound (20) which had a melting point of 105°–106.5° C.

Elemental analysis—Calcd.—C: 42.63%, H: 3.58%, N: 21.31%. Found—C: 42.55%, H: 3.41%, N: 21.53%.

PREPARATION EXAMPLE 7

[Compound (21)]

To 3.4 g of N-hydroxypyridine was added 20 ml of DMF to dissolve the former. Then, 4.2 ml of triethylamine was added thereto. Temperature of the solution was reduced to 5° C., 5.8 g of p-toluenesulfonyl chloride was slowly added and reaction was effected at 5° C. for 30 minutes.

After the reaction, 200 ml of ice water was added and separated oil as rubbed by a spatula to precipitate white crystals. The crystals were filtered out, well washed with cold water and then dried under reduced pressure.

Yield 6.8 g Melting point 98°–99.5° C.

Elemental analysis—Calcd.—C: 54.33%, H: 4.18%, N: 5.28%. Found—C: 54.26%, H: 4.00%, N: 5.32%.

PREPARATION EXAMPLE 8

[Compound (22)]

6.9 g of imidazole was dissolved in 80 ml of dioxane. Then, 6.3 g of methanesulfonyl chloride was added dropwise thereto and after completion of the addition the mixture was stirred at room temperature for 2 hours.

After the reaction the precipitated salt was filtered off, the precipitate was concentrated under reduced pressure and 40 ml of benzene was added to effect recrystallization to obtain 5.8 g of compound (22) which had a melting point of 68°–70° C.

Elemental analysis—Calcd.—C: 32.87%, H: 4.14%, N: 19.17%. Found—C: 32.61%, H: 4.23%, N: 19.01%.

The process for hardening gelatin according to this invention includes all forms of contact reactions of said compounds represented by the general formula with gelatin. Especially, in the case of allowing said compounds to act with gelatin in gelatin films which are constitutive layers of photographic light sensitive materials, there are the following methods: adding the compounds to a coating liquid for gelatin-containing layers, coating the liquid and drying the layer; adding preliminary reaction products of the compounds and gelatin to a coating liquid for layers, then coating the liquid and drying the layer; coating the liquid containing the compounds on gelatin layers and drying it; dipping gelatin layers in a solution of the compounds; dipping gelatin layers in a solution of the compound before or during developing treatment.

When the hardeners of this invention are added to a coating liquid for forming gelatin films, amount of the hardeners to be added may vary depending on kind, physical properties and photographic characteristics of the gelatin films, but generally 0.01–100% by weight, preferably 0.1–10% by weight based on the dry weight of gelatin. The hardener may be added at any stage of preparation of coating liquid for formation of gelatin films. However, when it is added to a silver halide emulsion, preferably it is added after second digestion of the silver halide emulsion, more preferably immediately before coating.

The hardeners of this invention have no hygroscopic property and decomposition property and so they do not deteriorate at all even over a long period of storage at room temperature. Furthermore, they have good solubility in water, alcohols, etc.

When the hardeners of this invention are applied to gelatin films of silver halide photographic light sensitive materials, they exhibit effective hardening property without damaging photographic characteristics of the photographic emulsions such as fog, sensitivity, etc. Furthermore, since they cause little after-hardening with lapse of time, photographic light sensitive materials of stable quality can be obtained and furthermore they have no adverse effect on the photographic emulsions even for a long period of storage of the materials, give effective stability to the materials and provide excellent hardening property which can sufficiently stand high temperature and rapid processing and automatic processing.

The hardeners of this invention may be used singly and, if necessary, two or more of them may be used in combination. Furthermore, they may also be combined with the previously mentioned known hardeners and the like.

As examples of silver halide photographic light sensitive materials to which this invention can be applied may be mentioned those for any of black and white, color and pseudo color photographic processes, those for various ones such as general photography, printing, X-ray, radiography, etc. and those for negative, positive and diffusion transfer processes.

Gelatins to which the hardeners of this invention are applied may be, if necessary, partly replaced with colloidal albumin, casein, cellulose derivatives such as carboxymethylcellulose, hydroxyethylcellulose, etc., agar, sodium alginate, starch derivatives, synthetic hydrophilic colloids such as polyvinyl alcohol, poly-N-vinyl pyrrolidone, polyacrylic acid copolymer, polyacrylamide or their derivatives or partial hydrolyzates. Furthermore, they may be replaced with so-called gelatin derivatives, namely, those which are obtained by treating and modifying amino group, imino group, hydroxy group, carboxyl group contained as functional groups in molecule with agents having one group capable of reacting with said groups or graft polymers to which molecular chain of other high molecular materials is bonded.

The light sensitive components of the silver halide photographic materials may be any of the known silver halides such as silver chloride, silver iodide, silver bromide, silver iodobromide, silver chlorobromide, silver chloroiodobromide and the like. The emulsion may be subjected to various chemical sensitizations such as sensitization with salts of noble metals such as ruthenium, palladium, rhodium, platinum, gold, etc., sulfur sensitization with sulfur compounds, selenium sensitization with selenium compounds, reduction sensitization with tin (II) salts, polyamines, etc., sensitization with polyalkyleneoxide compounds. Furthermore, the emulsion may also be optically sensitized with cyanine dyes, merocyanine dyes, etc. Moreover, the emulsions may contain various known photographic additives, e.g., stabilizers such as triazole compounds, azaindene compounds, benzothiazolium compounds, etc., wetting agents such as dihydroxyalkanes, etc., antistatic agents, ultraviolet absorbing agents, water dispersible particulate high molecular substances obtained by emulsion polymerization, coating assistants such as saponin, polyethylene glycol lauryl ether, sodium dodecylbenzenesulfonate, fluorine type surfactants such as those disclosed in Japanese Patent Publications (Kokoku) Nos. 9303/72 and 43130/73.

As the supports for the photographic light sensitive materials to which the method for hardening of this invention is applied may be used, for example, films or sheets such as papers, laminate papers, glasses, cellulose acetate, cellulose nitrate, polyesters, polyamides, polystyrene, etc.

The following examples are illustrative of this invention.

EXAMPLE 1

A silver iodochlorobromide gelatin emulsion having the composition of silver bromide 65.5 mole %, silver chloride 34.0 mol % and silver iodide 0.5 mol % and an average particle size of 0.45 μm was prepared by neutral single jet method. After physical digestion, the emulsion was desalted by washing with water, then gelatin was added and then sodium thiosulfate was added to effect chemical sensitization. Thereafter, a stabilizer and a surfactant were added to obtain a finished emulsion. Thus obtained gelatin-silver halide emulsion was divided into 18 portions. To each of 1-15 portions was added the exemplified compound as shown in Table 1 in an amount of 0.2 millimol per 1 g of gelatin. The other 3 portions were used for comparison and to one of them was added formaldehyde (Comparative A), and to one of the other two was added the compound represented by

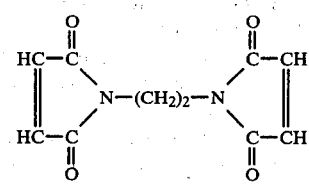

(Comparative B) in an amount of 0.2 millimol per 1 g of gelatin, respectively, and to the remaining one was added no hardener (Comparative C). Thus obtained 18 emulsions were coated on photographic paper bases both surfaces of which were coated with polyethylene layers in such an amount as 3.0 g/m² as silver nitrate and 5.0 g/m² as gelatin and these were dried. Thus obtained samples were kept at 40° C. for 5 days.

A part of each sample was exposed through a step wedge and thereafter was developed with developing solution having the following composition at 20° C. for 120 seconds, stopped, fixed, water-washed and dried. Photographic characteristics thereof were measured.

| Developing solution | |
|---|---|
| Water | 750 ml |
| Metol | 1.0 g |
| Hydroquinone | 4.0 g |
| Sodium sulfite | 15.0 g |
| Sodium carbonate (monohydrate) | 26.7 g |
| Potassium bromide | 0.7 g |
| Water to make | 1,000 ml |

Another part of each sample was developed with the above mentioned developing solution at 20° C. for 10 minutes without exposure to determine fog.

The results obtained are shown in Table 1.

TABLE 1

| Sample No. | Compounds | Gamma | Maximum density | Fog |
|---|---|---|---|---|
| ① | (1) | 2.70 | 2.10 | 0.03 |

TABLE 1-continued

| Sample No. | Compounds | Gamma | Maximum density | Fog |
|---|---|---|---|---|
| ② | (3) | 2.80 | 2.18 | 0.03 |
| ③ | (4) | 2.90 | 2.20 | 0.04 |
| ④ | (6) | 2.90 | 2.20 | 0.03 |
| ⑤ | (7) | 2.65 | 2.10 | 0.02 |
| ⑥ | (9) | 2.60 | 2.00 | 0.04 |
| ⑦ | (12) | 2.75 | 2.15 | 0.03 |
| ⑧ | (13) | 2.70 | 2.10 | 0.02 |
| ⑨ | (16) | 2.80 | 2.18 | 0.04 |
| ⑩ | (17) | 2.90 | 2.20 | 0.03 |
| ⑪ | (19) | 2.80 | 2.20 | 0.03 |
| ⑫ | (20) | 2.85 | 2.20 | 0.02 |
| ⑬ | (22) | 2.70 | 2.10 | 0.04 |
| ⑭ | (23) | 2.60 | 2.00 | 0.03 |
| ⑮ | (24) | 2.75 | 2.10 | 0.03 |
| ⑯ | Comparative A | 2.40 | 1.90 | 0.06 |
| ⑰ | Comparative B | 2.30 | 1.80 | 0.03 |
| ⑱ | Comparative C (none) | 3.0 | 2.30 | 0.04 |

As is clear from the above results, the compounds of this invention causes only a little reduction in maximum density and softening of tone (decrease of gamma value) and only a small fogging which gave no deleterious effect on photographic characteristics.

EXAMPLE 2

A part of each of the 18 samples obtained in the same manner as in Example 1 was dipped in the same developing solution as of Example 1 and heated to measure the temperature at which the emulsion film was dissolved out to obtain a melting point which was standard for hardness of films. The remaining part of each of said samples was dipped in said developing solution at 20° C. for 120 seconds and then a ball-pointed needle of 0.5 mm in diameter kept perpendicularly on the film surface was moved at a speed of 1 cm/sec under a load and the mechanical strength of the film was expressed by the load (in grams) under which the film surface was damaged. The results are shown in Table 2.

TABLE 2

| Sample No. | Melting point(°C.) | Mechanical strength (g) | Sample No. | Melting point(°C.) | Mechanical strength (g) |
|---|---|---|---|---|---|
| ① | 92 | 180 | ⑩ | 89 | 163 |
| ② | 91 | 165 | ⑪ | 93 | 220 |
| ③ | 91 | 173 | ⑫ | 87 | 175 |
| ④ | 90 | 195 | ⑬ | 92 | 180 |
| ⑤ | 90 | 160 | ⑭ | 93 | 230 |
| ⑥ | 93 | 225 | ⑮ | 92 | 190 |
| ⑦ | 89 | 163 | ⑯ | 90 | 80 |
| ⑧ | 90 | 160 | ⑰ | 80 | 20 |
| ⑨ | 92 | 168 | ⑱ | 28 | 20 |

As is clear from Table 2, the compounds of this invention had very excellent hardening effect.

What is claimed is:

1. A process for hardening gelatin, characterized by reacting gelatin with a compound represented by the following general formula:

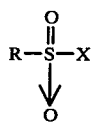

where R represents an alkyl or aryl group and X represents an oxy group represented by —O—R₁ wherein R₁ is a pyridyl group represented by

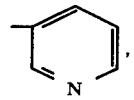

or a quaternary salt thereof represented by

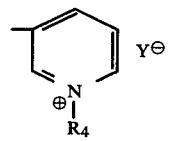

these pyridyl group and quaternary salt thereof may be substituted with an alkyl, aryl, aralkyl, carboxyl or a group containing the same or a sulfo group or a group containing the same, $Y^\ominus$ is not present when they are substituted with a carboxyl group, sulfo group or group containing carboxyl or sulfo group, $R_4$ is an alkyl group or aralkyl group and when $R_4$ contains a sulfo group or carboxyl group, $Y^\ominus$ is not present and $Y^\ominus$ is an anion.

2. A gelatin-silver halide photographic emulsion which contains a compound represented by the following general formula:

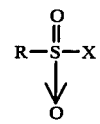

where R represents an alkyl or aryl group and X represents an oxy group represented by —O—R₁ wherein R₁ is a pyridyl group represented by

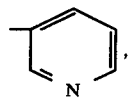

or a quaternary salt thereof represented by

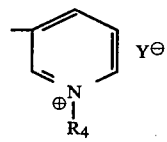

these pyridyl group and quaternary salt thereof may be substituted with an alkyl, aryl, aralkyl, carboxyl or a group containing the same or a sulfo group or a group containing the same, $Y^\ominus$ is not present when they are substituted with a carboxyl group, sulfo group or group containing carboxyl or sulfo group, $R_4$ is an alkyl group or aralkyl group and when $R_4$ contains a sulfo group or carboxyl group, $Y^\ominus$ is not present and $Y^\ominus$ is an anion.

3. A gelatin-silver halide photographic emulsion according to claim 2 wherein the amount of the compound is 0.1–10% by weight based on the dry weight of gelatin.

4. A photographic light sensitive material which comprises a support having thereon at least one gelatin-containing layer which is hardened with a compound represented by the following general formula:

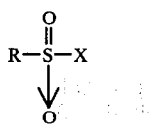

where R represents an alkyl or aryl group and X represents an oxy group represented by —O—$R_1$ wherein $R_1$ is a pyridyl group represented by

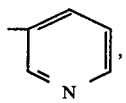

or a quaternary salt thereof represented by

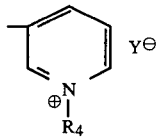

these pyridyl group and quaternary salt thereof may be substituted with an alkyl, aryl, aralkyl, carboxyl or a group containing the same or a sulfo group or a group containing the same, $Y^\ominus$ is not present when they are substituted with a carboxyl group, sulfo group or group containing carboxyl or sulfo group, $R_4$ is an alkyl group in aralkyl group and when $R_4$ contains a sulfo group or carboxyl group, $Y^\ominus$ is not present and $Y^\ominus$ is an anion.

5. A process for providing a photographic light sensitive material comprising a support having thereon at least one gelatin-containing layer in which the gelatin containing layer is contacted with a compound represented by the following general formula:

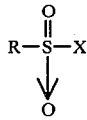

where R represents an alkyl or aryl group and X represents an oxy group represented by —O—$R_1$ wherein $R_1$ is a pyridyl group represented by

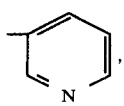

or a quaternary salt thereof represented by

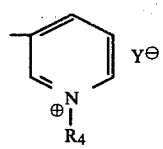

these pyridyl group and quaternary salt thereof may be substituted with an alkyl, aryl, aralkyl, carboxyl or a group containing the same or a sulfo group or a group containing the same, $Y^\ominus$ is not present when they are substituted with a carboxyl group, sulfo group or group containing carboxyl or sulfo group, $R_4$ is an alkyl group or aralkyl group and when $R_4$ contains a sulfo group or carboxyl group, $Y^\ominus$ is not present and $Y^\ominus$ is an anion.

6. A process according to claim 5 wherein the gelatin-containing layer is coated with a solution of the compound and then the layer is dried.

7. A process according to claim 5 wherein the gelatin-containing layer is dipped in a solution of the compound and then the layer is dried.

8. A process according to claim 5 wherein the compound is incorporated in a coating liquid containing gelatin, the liquid is coated on a support and then the layer is dried.

9. A process according to claim 5 wherein a preliminary reaction product of the compound and gelatin is incorporated in a coating liquid, the liquid is coated on a support and then the layer is dried.

10. A process according to claim 7 wherein the dipping of the layer in the solution is carried out before or during developing treatment.

11. A process according to claim 5 wherein the compound is used as hardener in a coating solution for the layer in an amount of 0.1–10% by weight based on dry weight of gelatin.

12. A photographic light sensitive material according to claim 4, wherein R in the general formula is an alkyl group of 1 to 5 carbon atoms.

13. A photographic light sensitive material according to claim 4, wherein $R_4$ is an alkyl, sulfoalkyl or carboxyalkyl group where the alkyl group has 1 to 5 carbon atoms.

14. A photographic light sensitive material according to claim 4, wherein R is an alkyl group of 1 to 5 carbon atoms and $R_4$ is an alkyl, sulfoalkyl or carboxyalkyl group where the alkyl group has 1 to 5 carbon atoms.

15. A photographic light sensitive material according to claim 4 wherein the compounds is

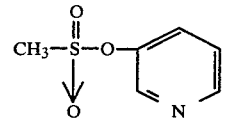

16. A photographic light sensitive material according to claim 4 wherein the compound is

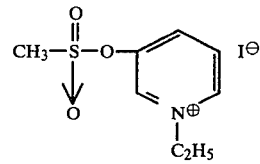

17. A photographic light sensitive material according to claim 4 wherein the compound is
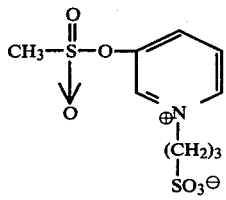
18. A photographic light sensitive material according to claim 4 wherein the compound is
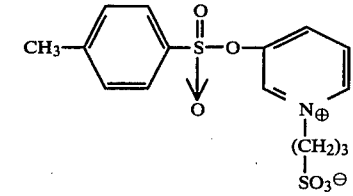
19. A photographic light sensitive material according to claim 4 wherein the compound is
* * * * *